United States Patent [19]
Lentini et al.

[11] Patent Number: 5,503,824
[45] Date of Patent: Apr. 2, 1996

[54] SKIN TANNING COMPOSITIONS

[76] Inventors: Peter Lentini, 263-45 74th Ave., Glen Oaks, N.Y. 11004; Kenneth Marenus, 62 McCulloch Dr., Dix Hills, N.Y. 11746; Neelam Muizzuddin, 100 Cherry St., Farmingdale, N.Y. 11735; Edward Pelle, 140 Meyer Ave., Valley Stream, N.Y. 11580; Louis Punto, R. P. Sherer, Inc. 2725 Sherer Dr. North, St. Petersburg, Fla. 33716-1016

[21] Appl. No.: 164,519

[22] Filed: Dec. 9, 1993

[51] Int. Cl.⁶ ........................... A61K 7/42
[52] U.S. Cl. ........................... 424/59
[58] Field of Search ................... 424/59

[56] References Cited

U.S. PATENT DOCUMENTS

| | | | |
|---|---|---|---|
| 2,949,403 | 8/1960 | Andreadis | 424/59 |
| 3,177,120 | 4/1965 | Black et al. | 424/59 |
| 3,864,473 | 2/1975 | Ciaudelli | 424/60 |
| 4,145,413 | 3/1979 | Usdin et al. | 424/63 |
| 4,522,807 | 6/1985 | Kaplan | 424/59 |
| 4,708,865 | 11/1987 | Turner | 424/59 |

FOREIGN PATENT DOCUMENTS

| | | | |
|---|---|---|---|
| 0275719 | 7/1988 | European Pat. Off. | 424/59 |
| 0547864 | 6/1993 | European Pat. Off. | 424/59 |

OTHER PUBLICATIONS

Strykh et al., "Purification and Properties of Dinydroxyacetone Kinase from the Methylotrophic Yeast Candida Boidini", Institute of Biochemistry and Physiology of Microorganisms, USSR Academy of Sciences: Pushchino (1983) No Translation.

Felix et al., "Erneute Untersuchungen Über die chemische Struktur von Protaminen", Chemische Struktur von Protaminen (1963) No Translation.

*Primary Examiner*—Shelley A. Dodson
*Assistant Examiner*—Michael A. Williamson

[57] ABSTRACT

The disclosed invention is directed to methods and compositions for improving the rate, extent and lifetime of an artificially induced tanning of the human skin. The invention entails treating the skin with agents such as amino acids, dipeptides, and amino substituted containing polymers either prior to or simultaneously with application of dihydroxyacetone.

24 Claims, No Drawings

SKIN TANNING COMPOSITIONS

FIELD OF THE INVENTION

The invention generally relates to the field of cosmetic compositions. More particularly, the invention relates to compositions and preparations which are applicable to the human skin for imparting thereto a simulated tan such as would be normally acquired by exposure to the sun.

BACKGROUND OF THE INVENTION

Many individuals have a skin complexion which does not tan readily on exposure to sun light. Others achieve a tan only with great discomfort and possibly adverse effects to the skin due to exposure to the suns rays. Yet attainment of a tan by many individuals is highly desired for cosmetic and other reasons, especially if this can be accomplished without the usual exposure to the sun.

In other instances, individuals who tan with difficulty may desire to extend the life of a naturally acquired tan without re-exposure to the sun. Also, a skin tan may be desired when weather conditions do not permit the Usual exposure to the sun in order the acquire a tan.

Acquisition of a natural tan by exposure to the sun, however, may be almost impossible for those very light skinned persons who tend to burn rather than tan. In addition, the deleterious effects of excessive exposure to sunlight are becoming more generally recognized.

One of the most common methods for artificially inducing a suntan is to subject the body to the rays of an ultraviolet ray lamp. While this induces a tan, it has many of the same disadvantages as tanning by the sun since many of the deleterious effects of sunlight are due to its ultraviolet radiation component. For instance, the increasing incidence of skin cancer has been attributed to increased exposure to ultraviolet radiation from the sun.

It is known in the art to induce an artificial tan by applying dihydroxyacetone ("DHA") to the human skin by a suitable vehicle or base. Darkening of the human skin occurs within about 2–24 hours after applying a suitable composition containing DHA as the active agent. See U.S. Pat. No. 2,949,403.

While DHA has been widely commercialized as a skin tanning agent, formulations containing DHA suffer from a number of deficiencies. A particular disadvantage is the time required to produce the desired tanning effect. A further disadvantage is that the tan imparted by DHA readily is washed off the skin. A need therefore exists for skin tanning formulations which more quickly produce the desired tanning effect. A further need exists for skin tanning formulations which are less readily be removed from the skin.

SUMMARY OF THE INVENTION

The disclosed invention is directed to methods and compositions for improving the rate, extent and lifetime of an artificially induced tan of the human skin. The invention entails treating the skin with amino containing agents such as amino acids, dipeptides, and amine containing polymers either prior to, subsequent to, or simultaneously with application of DHA.

In accordance with the invention, a composition applicable to the human skin and which is suitable for imparting a tan thereto is provided. Preferably, the composition is in the form of a spray or an emulsion. The composition includes a component having DHA, and an amino containing component having at least one of an amino acid or a polymer having an amino substituent. The amino containing component can be any of amino acids, dipeptides, polypeptides, polyaziridines, or amino substituted silicones of formula I:

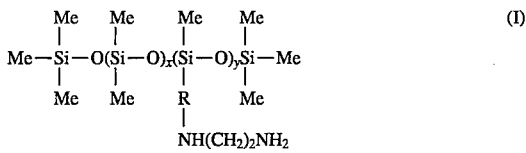

where:
x=48–148
y=3–15 and
R is a divalent alkylene radical of 3–6 carbon atoms

The amino substituted silicones of Formula (I) are available from Dow Corning under the name DCX28124. The amino containing component is capable of reacting with the first component to increase the rate and degree of tan imparted to the human skin.

The invention also is directed to a method for increasing the rate of artificially tanning the human skin and retention of that tan by applying to the skin a composition containing amino groups prior or simultaneously with application of DHA. The amino groups can be provided in the form of amino acids, dipeptides, polypeptides, or amino substituted silicones of the above formula (I). Amino substituted polymers containing primary, optionally secondary, optionally tertiary substituted amino groups can be employed. These polymers are exemplified by polyaziridines such as polyethyleneimine and the like.

In yet another aspect of the invention, a cosmetic preparation applicable to the human skin for imparting a tan within fifteen minutes after application thereto is provided.

DETAILED DESCRIPTION OF THE INVENTION

Generally, and in accordance with the invention, the rate and degree of artificial tanning imparted to the human skin by DHA, as well as the lifetime of that tan, surprisingly can be increased by treating the skin with selected amino containing compounds prior to, subsequent to, or simultaneously with applying DHA containing compositions.

In a first embodiment of the invention, an amino acid is applied to the skin prior to, or simultaneously with application of a composition comprising DHA. The amino acid can be applied to the skin as a hydroalcoholic solution. DHA can be applied as a hydroalcoholic spray, as a mixture of DHA in an oil in water emulsion, or as an aqueous, oil-free, alcohol-free spray-on emulsion.

A variety of amino acids may be employed to treat the skin. These amino acids include but are not limited to alanine, arginine, aspartic acid, asparagine, cystine, glutamine, glutamic acid, glycine, histidine, isoleucine, leucine, lysine, methionine, phenylalanine, serine, threonine, tryptophan, tyrosine, valine, and the like, preferably, glycine, tryptophane, and lysine. The amino acids can be admixed with numerous solvents and solvent mixtures to provide solutions which may be applied to the skin prior to or simultaneously with application of DHA. These solvents and solvent solutions include water-alcohol mixtures wherein water may vary from 51 to 100% and the alcohol may vary from 0 to 50%. Preferably, water is the major component in the water-alcohol mixtures. The alcohols employed in these water-alcohol mixtures can include but are not limited to alkyl alcohols such as $C_2$–$C_{20}$ alcohols, preferably ethanol; $C_2$–$C_{10}$ glycols, preferably $C_2$–$C_4$ glycols.

The DHA composition in various vehicles can be applied to the skin subsequent to or simultaneously with applying the amino acid solutions. The DHA composition can be applied in the form of a spray of DHA in a hydroalcohol solution such as water-ethanol; an aqueous, oil-free, alcohol-free spray-on emulsion, or preferably as a cream in the form of DHA in an emulsion such as oil in water. Useful oils include silicone oils, mineral oils, as well as naturally derived or synthetic plant or animal oils. Examples of useful oils include but are not limited to dimethicone, sweet almond oil, rice oil, squalane, shark liver oil, mink oil, liquid oil esters, liquid oil ethers, diisopropyl adipate, and polypropylene glycol methyl ether.

The percentages of DHA in the vehicle can vary over a wide range. When employed in a spray, the amount of DHA typically is 1–20%, preferably 5–8%, based on the liquid vehicle of the spray. When employed as a cream of an oil in water emulsion, DHA typically is 1–20% preferably 5–8% based on the emulsion.

In examples 1–22 given in Table 1 below, the absorption effects attributable to reacting 0.5% aqueous solutions of amino acids with 1% DHA in a solution of water and ethanol with a water:ethanol ratio of 1:15 is measured. Various pH values of the amino acid solution are employed.

The chromogenic effect produced as a result of reaction of the amino acids with DHA for 16 hours is gauged by an ultra violet visible Hewlett Packard spectrophotometer model 8452A that measures the characteristic yellow/brown chromogen formed as a result of this reaction at 428 nm and then correcting for dilution. In making these measurements, solutions of the amino acids mixed with DHA are placed in a UV visible spectrophotometer and absorbance is quantified at 428 nm. The results given in Table 1 represent the percentage absorption measured at 428 nm. Higher absorbances indicate increased darkening.

TABLE 1

| EXAMPLE | Amino Acid | Absorbance at pH 4.0 | Absorbance at pH 7.0 | Absorbance at pH 10.0 |
| --- | --- | --- | --- | --- |
| 1 | alanine | 0 | 1.16 | 1.19 |
| 2 | arginine | 0 | 1.45 | 0 |
| 3 | aspartic acid | 0 | 0.92 | 0.38 |
| 4 | asparagine | 0 | 1.10 | 0 |
| 5 | cysteine | 0 | 0 | 0 |
| 6 | cystine | 0 | 0.23 | 1.74 |
| 7 | glutamine | 0 | 2.19 | 0.46 |
| 8 | glutamic acid | 0 | 0.08 | 0.63 |
| 9 | glycine | 0.02 | 5.90 | 3.24 |
| 10 | histidine | 0 | 0.80 | 0.42 |
| 11 | isoleucine | 0 | 0.96 | 1.17 |
| 12 | leucine | 0 | 1.09 | 1.51 |
| 13 | lysine | 0 | 2.85 | 2.91 |
| 14 | methionine | 0 | 1.65 | 0.79 |
| 15 | phenylalanine | 0 | 1.56 | 0.61 |
| 16 | proline | 0 | 0 | 0.25 |
| 17 | OH-proline | 0 | 0 | 0.03 |
| 18 | serine | 0 | 0.43 | 0 |
| 19 | threonine | 0 | 0.12 | 0 |
| 20 | tryptophan | 0.71 | 12.03 | 0.78 |
| 21 | tyrosine | 0 | 2.50 | 0.49 |

TABLE 1-continued

| EXAMPLE | Amino Acid | Absorbance at pH 4.0 | Absorbance at pH 7.0 | Absorbance at pH 10.0 |
| --- | --- | --- | --- | --- |
| 22 | valine | 0 | 1.13 | 1.49 |

In an alternative embodiment, dipeptides, tri-peptides and dipeptide mixtures of the amino acids of Table I can be applied to the skin. Generally, however, mixtures of dipeptides are employed. In examples 23–27 below, pretreatment mixtures of glycosaminoglycans (GAGS) and dipeptides of Glycine-Serine are evaluated for their ability to increase the tanning effects of DHA. Examples of GAGS useful in this invention include heparin sulfate, dermatan sulfates and chrondoiton sulfate. In examples 23–26, mixtures of chrondoiton sulfate and dipeptide are applied to the skin and absorbed for 10 minutes, and then dried by heating under a 500 watt infrared light bulb. The skin then is treated a second time under the same conditions with the same mixture for an additional ten minutes and dried under the 500 watt infrared light bulb. A composition comprising 5% DHA, 32% magnesium aluminosilicate, 21% water then is applied to the treated skin. For comparison, in Example 27, the same DHA composition is applied to an untreated portion of the skin. Tanning, gauged in terms of total color change ($\Delta E$) measured with a Minolta chromameter model No. CR200 before treatment, after 5 hours, and 24 hours is given in Table 2.

TABLE 2

| Example | Pretreatment Composition | Percent of Dipeptide in Composition | $\Delta E^1$ -- 5 hours | $\Delta E^1$ -- 24 hours |
| --- | --- | --- | --- | --- |
| 23 | 2 gm chondroitin sulfate B solution$^2$ + 0.05 gm dipeptide$^3$ | 2.4 | 5.43 | 4.97 |
| 24 | 2 gm chondroitin sulfate B solution$^2$ + 0.1 gm dipeptide$^3$ | 4.8 | 5.83 | 4.54 |
| 25 | 2 gm chondroitin sulfate B solution$^2$ + 0.5 gm dipeptide$^3$ | 20.0 | 6.36 | 4.23 |
| 26 | 2 gm chondroitin sulfate B solution$^2$ + 1.00 gm dipeptide$^3$ | 33.0 | 7.41 | 4.9 |
| 27 | None | | 5.23 | 6.25 |

$^1\Delta E = \sqrt{(\Delta L)^2 + (\Delta a)^2 + (\Delta b)^2}$
where $\Delta L$ is the decrease in reflectance compared to the baseline skin color, $\Delta a$ is the increase in red coloration compared to the baseline skin color, and $\Delta b$ is the increase in yellow coloration compared to the baseline skin color.
$^2$Solution formed by dissolving 100 milligrams of Chondroitin Sulfate B (Sigma Chemical Company, St. Louis, MO) in one millimeter of 6 millimolar aqueous Glycine-L-Serine (Sigma) solution.
$^3$Glycine-Serine solution formed by dissolving one gram of Glycine-L-Serine (Sigma) in 3 grams Heparasome (commercial heparin sulfate liposome preparation available commercially from Bioetica, Inc., Westbrook, ME).

In a further embodiment of the invention as illustrated in examples 28–32, polyethyleneimine and a polypeptide of lysyl-P-glutamic-cysteamine are applied to the skin prior to application of DHA. DHA is applied as a mixture of 5%

DHA, 21% water, and 32% magnesium alumino-silicate. The polyethyleneimines employed have the formula (II):

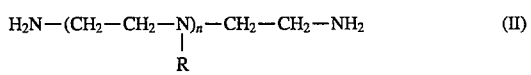

wherein:

R=H or $CH_2$—$CH_2$—NH—$CH_2$—$NH_2$;

and n is an integer chosen such that the molecular weight of the polyethyleneimine is between 500 and 2,000,000, preferably between 400,000 and 800,000, most preferably between 500,000 and 700,000. These polyethyleneimines are commercially available from a number of suppliers. For example, polyethyleneimines are sold by BASF Corporation (Parsippany, N.J.), under the tradename Polymin®.

Polyethyleneimine is a polyaziridine. Polyaziridines other than polyethyleneimine can be employed. Examples of useful polyaziridines include but are not limited to polyethyleneimine and the like. The amino containing polymers may be diluted in water-alcohol solutions such as water-ethanol to concentrations as low as 2%. The polymers also may be applied in neat form.

A variety of polypeptides other than lysyl P glutamic cysteamine also may be employed. Examples of useful polypeptides include combinations of two or more of the amino acids given in Table 1. Examples include but are not limited to alanine-arginine, alanine-arginine-asparagine, and the like. The peptide chains may be diluted in water-alcohol solutions such as water-ethanol, or they may be employed in neat form.

In examples 28–31, areas of skin are treated with solutions of polyethyleneimine or lysyl P glutamic cysteamine and absorbed for 50–60 minutes. Then, a thin layer of the composition having 5% DHA employed in examples 20–31 is applied to the treated skin. For comparison, in Example 32, the same 5% DHA composition is applied to an untreated portion of skin. Skin tanning in terms of increase in skin color is measured with the chromameter described above before treatment to obtain baseline data, and after 5 hours, 24 hours and 5 days after treatment. The results are given in Table 3.

TABLE 3

| Example | Composition | $\Delta E^1$ -- 5 hours | $\Delta E$ -- 24 hours |
|---|---|---|---|
| 28 | Polyethylene imine polymer[2] 5% dilution[3] | 6.7 | 7.7 |
| 29 | Polyethylene imine polymer[2] no dilution | 13.9 | 6.8 |
| 30 | Lysyl-p glutamic Cysteamine 5% dilution | 5.7 | 6.49 |
| 31 | Lysyl-p glutamic Cysteamine no dilution | 5.6 | 6.2 |
| 32 | DHA only | 5.12 | 5.5 |

[1] $\Delta E = \sqrt{(\Delta L)^2 + (\Delta a)^2 + (\Delta b)^2}$
where $\Delta L$ is the decrease in reflectance compared to the baseline skin color, $\Delta a$ is the increase in red coloration compared to the baseline skin color, and $\Delta b$ is the increase in yellow coloration compared to the baseline skin color.
[2] Polymin ®P, a 50% aqueous solution of a polyethyleneimine of the above Formula (II) with an approximate molecular weight of 600,000 from BASF Co.
[3] Ethyleneimine Polymer at 5% dilution in 1:1 ethanol-water solution, final concentration of 0.5%.

In examples 28–31, the amino containing material (polyethyleneimine) is applied to the skin prior to applying the DHA containing composition. In examples 33–34, the amino containing material is applied to the skin as a mixture of the amino containing material and a hydroalcoholic solution (EL Self Protection Tonic, available from Estee Lauder, Inc.), prior to applying the DHA containing material. The effects of including the amino containing material in the EL Self Protection Tonic are shown in Table 4 below. The tanning effect is determined in the manner given above. For comparison, in Examples 35 and 36, the tanning effects of the EL Self Action Tanning Cream (Medium) and DHA containing compositions on untreated skin are measured.

TABLE 4

| Example | Composition | $\Delta E^1$ -- 1 hour | $\Delta E$ -- 2 hour | $\Delta E$ -- 3 hour | $\Delta E$ -- 4 hour | $\Delta E$ -- 5 hour |
|---|---|---|---|---|---|---|
| 33 | treated with polyethyleneimine,[2] and then with water in silicone DHA cream[3] | 1.5 | 2.75 | 3.69 | 4.33 | 5.59 |
| 34 | treated with polyethyleneimine,[2] and then with EL Self Action Tanning Protection Cream (Medium)[4] | 2.13 | 3.32 | 4.12 | 5.28 | 6.66 |
| 35 | EL Self Action Tanning Cream (Medium)[4] | 1.18 | 1.89 | 3.5 | 3.91 | 5.11 |
| 36 | Water in silicone DHA cream[3] | 1.06 | 2.29 | 3.9 | 4.25 | 5.14 |

[1] $\Delta E = \sqrt{(\Delta L)^2 + (\Delta a)^2 + (\Delta b)^2}$

TABLE 4-continued

| Example | Composition | $\Delta E^1$ -- 1 hour | $\Delta E$ -- 2 hour | $\Delta E$ -- 3 hour | $\Delta E$ -- 4 hour | $\Delta E$ -- 5 hour |
|---|---|---|---|---|---|---| where $\Delta L$ is the decrease in reflectance compared to the baseline skin color, $\Delta a$ is the increase in red coloration compared to the baseline skin color, and $\Delta b$ is the increase in yellow coloration compared to the baseline skin color.
[2]Polyethyleneimine of molecular weight of 50,000–100,000 Dalton, 20% dilution in EL Full Strength Self Protection Tonic.
[3]Cream Composition comprises 5% DHA, 16.7% cyclomethicone, 15% of a copolyol of cyclomethicone and dimethicone, 60.4%, deionized water 2% NaCl, and other cosmetic ingredients.
[4]Available from Estee Lauder

EXAMPLE 37–43

The compositions of Examples 37–43 further illustrate the invention. The compositions of examples 37–43 are made by dissolving each ingredient in order of appearance. These compositions require no special processing other than a prop mixer and an appropriately sized mixing vessel.

TABLE 5

| Exam. No./Constituent | 37 | 38 | 39 | 40 | 41 | 42 | 43 |
|---|---|---|---|---|---|---|---|
| Deionized Water | 79.00 | 78.00 | 79.00 | 78.00 | 0.00 | 0.00 | 0.00 |
| Polymin P | 4.00 | 0.00 | 0.00 | 0.00 | 0.00 | 0.00 | 0.00 |
| 1,3-B.[2] Glycol | 10.00 | 10.00 | 10.00 | 10.00 | 0.00 | 0.00 | 0.00 |
| Fragrance | 0.50 | 0.50 | 0.50 | 0.50 | Remainder | Remainder | Remainder |
| Tween 20, NF[3] | 0.50 | 0.50 | 0.50 | 0.50 | 0.00 | 0.00 | 0.00 |
| Liponic EG-1[4] | 5.00 | 5.00 | 5.00 | 5.00 | 0.00 | 0.00 | 0.00 |
| Ucon 50HB660[5] | 1.00 | 1.00 | 1.00 | 1.00 | 1.00 | 0.00 | 0.00 |
| Polymin G-20 | 0.00 | 5.00 | 0.00 | 0.00 | 0.00 | 0.00 | 0.00 |
| Polymin FG' | 0.00 | 0.00 | 0.00 | 5.00 | 0.00 | 0.00 | 0.00 |
| Polymin G-35' | 0.00 | 0.00 | 4.00 | 0.00 | 0.00 | 0.00 | 0.00 |
| Polymin Waterfree' | 0.00 | 0.00 | 0.00 | 0.00 | 2.00 | 0.00 | 2.00 |
| DC X2-8124 | 0.00 | 0.00 | 0.00 | 0.00 | 0.00 | 2.00 | 2.00 |
| Ceraphyl ICA[6] | 0.00 | 0.00 | 0.00 | 0.00 | 10.00 | 10.00 | 10.00 |
| DC Q2-1401[7] | 0.00 | 0.00 | 0.00 | 0.00 | 1.00 | 1.00 | 1.00 |
| DC 344[7] | 0.00 | 0.00 | 0.00 | 0.00 | 80.00 | 80.00 | 78.00 |
| DC 345[7] | 0.00 | 0.00 | 0.00 | 0.00 | 5.00 | 5.00 | 5.00 |
| DC 200/20cts[7] | 0.00 | 0.00 | 0.00 | 0.00 | 2.00 | 2.00 | 2.00 |

[1]Polymin P, G-20, FG, G-35, Waterfree; available from BASF
[2]1,3-B. Glycol from Robeco Chemicals
[3]Tween 20, NF from ICI - Polysorbate 20
[4]Liponic EG1 from Lipo Chemicals - Glysereth 23
[5]UCON 50-HB-660 from Amerchol - PPG-12-Butech-16
[6]Ceraphyl ICA is available from Van Dyk Isocetyl Alcohol
[7]DC X2-8124, 1401, 344, 345, 200/20cts from Dow Corning In examples 28–31, 33, and 34, the amino containing material is applied prior to treating with DHA. However, in an alternative embodiment, and as illustrated in Example 44 below, the amino containing material is applied simultaneously with DHA.

EXAMPLES 44–45

Duo phase compositions formed of an amino containing polymer such as polyethyleneimine with DHA containing compositions is shown in example 44. These duo phase compositions provide DHA in the first phase, and polyethyleneimine in the second phase. The first phase that contains DHA may include hydroalcohol sprays, aqueous, oil-free, alcohol-free spray-on emulsions, or oil in water emulsions. The relative percentages of the first and second phases in the duo phase composition may vary over a wide range. The amount of DHA in the first phase may vary from 1 to 20%, preferably 4 to 8%, of the duo phase composition. The second phase may include a gel that contains 10–100% polyethyleneimine.

The first and second phases are applied simultaneously to the skin. The surprising tanning effects attributable to use of the duo phase compositions is given below in Table 6. For comparison, and as shown in Example 45, the tanning effects due to commercially available, EL Self Action Tanning Medium containing DHA are provided.

TABLE 6

| Example | Composition | $\Delta E^1$ -- 5 hour | $\Delta E$ -- 24 hour |
|---|---|---|---|
| 44 | Duo phase[2] | 6.51 | 3.89 |
| 45 | EL Selftan Medium[3] | 5.23 | 3.90 |

[1]$\Delta E = \sqrt{(\Delta L)^2 + (\Delta a)^2 + (\Delta b)^2}$
where $\Delta L$ is the decrease in reflectance compared to the baseline skin color, $\Delta a$ is the increase in red coloration compared to the baseline skin color, and $\Delta b$ is the increase in yellow coloration compared to the baseline skin color.
[2]5% DHA, in first phase 5%; polyethyleneimine in second phase.
[3]Available from Estee Lauder.

From the foregoing description, one skilled in the art can easily ascertain the essential characteristics of this invention, and without departing from the spirit and scope thereof, can make various changes and modifications of the invention to adapt it to various usages and conditions.

We claim:
1. A cosmetic composition applicable to the human skin for imparting an artificial tan thereto comprising:

a first component comprising about 1–20 percent DHA; and a second component comprising at least about 2 percent of an amino-containing component selected from the group consisting of amino-substituted silicones and polyaziridines, wherein said second component is available for reaction with said first component to increase the rate and degree of tan imparted to the human skin.

2. The composition of claim 1 wherein said first component comprises at least one of either a water-alcohol solution, an aqueous, oil-free, alcohol-free spray-on emulsion, or an oil in water emulsion.

3. The composition of claim 2 wherein said water-alcohol solution comprises water and ethanol.

4. The composition of claim 2 wherein said DHA is about 5–8% of said first component.

5. The composition of claim 2 wherein said first component is an oil in water emulsion containing about 5–8% DHA.

6. The composition of claim 1, wherein said polyaziridine is polyethyleneimine.

7. The composition of claim 1 wherein said first component is an oil in water emulsion containing DHA and said second component is polyethyleneimine.

8. The composition of claim 1 wherein said first component is an oil in water emulsion containing DHA and said amino containing component is an amino substituted silicone.

9. The composition of claim 8 wherein said amino substituted silicone is a compound of Formula (I)

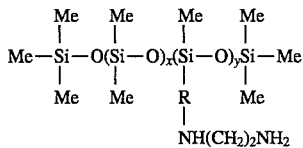

wherein:

x=48–148, y=3–15, and

R is a divalent alkylene radical of 3–6 carbon atoms.

10. A method of imparting an artificially induced tan to the human skin comprising:

treating the skin with a first composition having at least about 2 percent of an amino-containing component selected from the group consisting of amino-substituted silicones and polyaziridines therein; and applying to the skin a second composition having about 1–20 percent DHA therein.

11. The method of claim 10 wherein said first composition is at least one of either a water-alcohol solution or an oil-in-water emulsion.

12. The method of claim 11 wherein said water-alcohol solution is water ethanol.

13. The method of claim 10 wherein DHA is at least about 1% of said second composition.

14. The method of claim 10 wherein said DHA is about 5–8% of said second composition.

15. The method of claim 10 wherein said second composition is an oil in water emulsion containing about 5–8% DHA.

16. The method of claim 10 wherein said polyaziridine is polyethyleneimine.

17. The method of claim 10 wherein said first composition includes polyethyleneimine and said second composition is a water-in-oil emulsion containing DHA.

18. The method of claim 10 wherein said first composition comprises an amino substituted silicone of Formula (I)

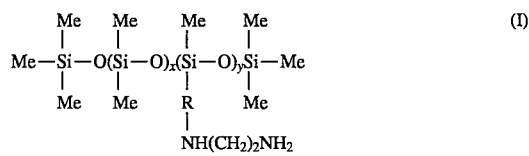

where:

x=8–148 y=3–15 and

R is a divalent alkylene radical of 3–6 carbon atoms and said second composition is a water-in-oil emulsion containing DHA.

19. The method of claim 10 wherein said treating with said first composition and said applying of said DHA containing composition is performed substantially simultaneously.

20. The method of claim 10 wherein said first and second compositions are applied simultaneously.

21. The method of claim 10 wherein said first and second compositions are in a duo phase composition.

22. A method of imparting an artificially induced tan to the human skin comprising:

(a) treating the skin with a first composition comprising at least about 2 percent of amino-containing component selected from the group consisting of an amino substituted silicone, or at least one polyaziridine; and (b) applying to the skin a second composition having about 1–20 percent DHA therein.

23. The method of claim 22 wherein said first and second compositions are applied simultaneously.

24. The method of claim 22 wherein said first and second compositions are in a duo phase composition.

* * * * *